United States Patent
Cunanan

[19]

[11] Patent Number: 6,024,920
[45] Date of Patent: Feb. 15, 2000

[54] MICROPLATE SCANNING READ HEAD

[75] Inventor: Chris Cunanan, Moraga, Calif.

[73] Assignee: Bio-Rad Laboratories, Inc., Hercules, Calif.

[21] Appl. No.: 09/291,787

[22] Filed: Apr. 14, 1999

Related U.S. Application Data

[60] Provisional application No. 60/082,570, Apr. 21, 1998.

[51] Int. Cl.[7] .......................... G01N 21/01; G01N 21/59
[52] U.S. Cl. .......................... 422/65; 422/82.09; 356/73; 356/432; 435/288.7
[58] Field of Search .................... 422/65, 82.08, 422/82.09; 435/288.4, 288.7; 356/73, 432, 440, 434

[56] References Cited

U.S. PATENT DOCUMENTS

| | | |
|---|---|---|
| 3,736,432 | 5/1973 | Sweet . |
| 4,240,751 | 12/1980 | Linnecke et al. ..................... 422/102 |
| 4,358,203 | 11/1982 | Citrin ..................................... 356/432 |
| 5,169,601 | 12/1992 | Ohta et al. ........................... 422/82.09 |
| 5,244,630 | 9/1993 | Khalil et al. ............................ 422/52 |
| 5,580,524 | 12/1996 | Forrest et al. . |
| 5,674,743 | 10/1997 | Ulmer . |
| 5,689,110 | 11/1997 | Dietz et al. . |
| 5,853,666 | 12/1998 | Seaton et al. . |
| 5,892,577 | 4/1999 | Gordon ............................... 422/82.09 |

*Primary Examiner*—Jeffrey Snay
*Attorney, Agent, or Firm*—David G. Beck; Townsend and Townsend and Crew, LLP

[57] ABSTRACT

A scanning head assembly is provided, the scanning head suited for use with instruments that characterize the absorption, fluorescence, and/or luminescence properties of one or more samples contained within a sample plate or microplate. The scanning head assembly is coupled to a pair of scanning mechanisms, thereby allowing the head assembly to be raster scanned along both the x- and y-axis. Although the scanning preferably follows a serpentine pattern, other scan patterns can be utilized. Single or multiple measurements can be made per sample well, multiple measurements either being reported individually or averaged together. Although the scanning head assembly can utilize a variety of configurations, in the preferred embodiment the scanning head assembly has a C-shape with the light source and associated optics mounted in the lower arm of the assembly and the detector and associated optics mounted in the upper arm. Preferably the optics associated with the source include one or more optical filters that regulate the wavelength of light radiating the sample.

21 Claims, 4 Drawing Sheets

MICROPLATE SCANNING READ HEAD

CROSS-REFERENCES TO RELATED APPLICATIONS

This application claims benefit of U.S. Provisional Patent Application Ser. No. 60/082,570, filed Apr. 21, 1998, the disclosure of which is incorporated herein by reference for all purposes.

FIELD OF THE INVENTION

The present invention relates generally to microplate reading systems, and more particularly, to a method and apparatus for scanning a microplate in order to determine the fluorescence, luminescence, and/or absorption in each sample well of the microplate.

BACKGROUND OF THE INVENTION

Bio-chemical researchers involved in high throughput screening and/or drug and chemical development require the capability to characterize millions of samples accurately and rapidly. Due to this requirement, sample testing is often performed in sample plates that may include tens, hundreds, or even thousands of individual sample wells. The use of such multi-well sample plates simplifies automation of sample testing, assuming the necessary test equipment is compatible with multi-well sample plates.

In designing high throughput test apparatus, typically a variety of system constraints are considered. The first critical design parameter is the intended use of the test apparatus. For example, the apparatus may be designed to characterize a sample's absorption, luminescence, or fluorescence properties. Additionally, the test apparatus may be designed to be capable of testing more than one property. A second critical design parameter is the size and format of the sample plate. Currently there are a variety of available standard format sample plates containing varying numbers of sample wells and types. These sample plates typically have different external dimensions and may also have different sample well dimensions. Although most instruments are designed to handle only a specific sample plate format, some instruments are designed to handle a range of sample plate formats. A third design parameter that is typically taken into account is the size and design of the individual sample wells. For example, sample wells vary in size from microns in diameter as utilized in some chip sample plates to millimeter sized wells or larger. Additionally, sample wells may be of varying depth, comprised of transparent or opaque materials, and utilize any of a variety of shapes, e.g., square or round cross-sections. Sample wells may also include a reflective bottom surface. Preferably an instrument is capable of handling a range of sample well types.

In a standard multi-well sample plate testing apparatus the sample plate is held within a holding fixture that is coupled to one or more scanning mechanisms. The scanning mechanisms allow the sample plate to be moved along at least one axis relative to the portion of the instrument used to characterize the sample (e.g., an excitation source and a fluorescence detector). Preferably the scanning mechanisms allow the sample plate to be moved along two axes, thus allowing a two-dimensional array of sample wells to be analyzed. Although moving the sample plate may cause problems such as sample spillage, typically these problems are minor in comparison to the difficulties associated with scanning the test head relative to a fixed sample plate. For example, to avoid sample spillage during plate movement, the plate can be moved at a slower rate and utilize gradual start and stop cycles. Additionally, the level of liquid within each sample well can simply be sufficiently below the top of the sample well to avoid spillage.

An instrument that provides the benefits of multi-well sample plate scanning without the drawbacks associated with translating the sample plate along multiple axes is desired. The present invention provides such an instrument.

SUMMARY OF THE INVENTION

The present invention provides a scanning head assembly for use in a variety of different instrument types. For example, the scanning head assembly of the present invention can be used to characterize the absorption, fluorescence, or luminescence properties of one or more samples. Preferably the instrument is capable of use with various microplate sizes and formats, thus providing maximum flexibility to the user.

In one aspect of the invention, the scanning head assembly has a C-shape with the light source mounted in one arm of the C-shaped assembly and the detector mounted in the other arm of the assembly. Preferably the source and associated optics are in the lower arm and the detector and associated optics are in the upper arm of the assembly. The invention can utilize other configurations as well, such as having the source in the upper arm and the detector in the lower arm. Alternatively, a non-C-shaped configuration can be used in which both the source and the detector are mounted within the same arm.

In another aspect of the invention, the scanning head assembly is coupled to a pair of scanning mechanisms that allow the head assembly to be raster scanned relative to a sample microplate along both the x- and y-axis. Although the scanning preferably follows a serpentine pattern, other scan patterns can be utilized. Single or multiple measurements can be made per sample well, multiple measurements either being reported individually or averaged together.

In another aspect of at least one embodiment of the invention, the source is a xenon flash lamp mounted within one arm of the head assembly. The light from the xenon lamp is conditioned and collimated with a series of apertures and lenses. Preferably the source light passes through a filter in order to limit the light wavelengths radiating the sample. The filter can be any of a variety of different filter types (e.g., bandpass, cutoff, etc.) and is preferably one of a series of filters accessible through a filter wheel or other filter selection system. Prior to irradiating the sample, a portion of the source light is separated using a beam splitter, the separated portion being used to monitor variations in the output of the source. The light from the sample passes through an aperture and is collected by a lens that focuses the sample light onto the measurement detector.

In another aspect of at least one embodiment of the invention, the scanning head assembly is coupled to a controller containing one or more processors. The controller is used to monitor and control the position of the scan head relative to the sample plate. The controller is also used during data collection and processing, lamp source control, and filter selection.

A further understanding of the nature and advantages of the present invention may be realized by reference to the remaining portions of the specification and the drawings.

DESCRIPTION OF THE SPECIFIC EMBODIMENTS

Figure 1:
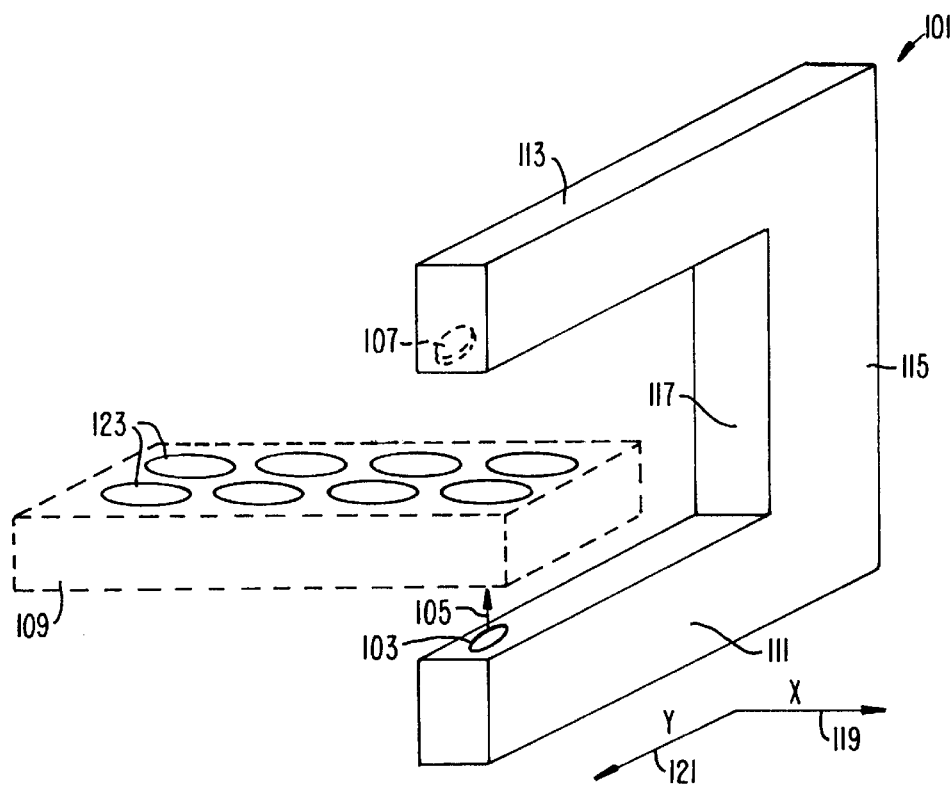
FIG. 1 schematically illustrates the basic apparatus according to the invention.

FIG. 1 schematically illustrates the basic apparatus according to the invention. The system is comprised of a read head 101 that is preferably C-shaped. The C-shape of read head 101 allows a source 103 radiating light in a direction 105 to be mounted within one arm of the head assembly and a detector 107 (shown in phantom) to be mounted within the second arm of the head assembly. It should be understood that although the illustrated configuration is preferred, in at least one embodiment the source and the detector are mounted in the same arm of the head assembly, thus eliminating the need for the C-shape of the assembly. Although placement of source 103 and detector 107 in opposite arms of read head 101 simplifies the optical constraints placed on the system, this configuration requires that the bottom surface of the sample well(s) be substantially transparent at the wavelengths of interest.

A sample plate, or microplate, 109 (shown in phantom) containing either a single sample well or multiple sample wells as shown fits between lower arm 111, upper arm 113, and back portion 115 of head assembly 101. Preferably source 103 and detector 107 are mounted near the ends of arms 111 and 113, respectively. The primary limitation on the size of plate 109 that can be read using head assembly 101 is the distance between the end portions of arms 111 and 113, i.e., the locations of source 103 and detector 107, and a front surface 117 of back portion 115.

Due to the compact design of head assembly 101, it can easily be moved relative to sample plate 109 along both x-axis 119 and y-axis 121. Moving head assembly 101 rather than the sample plate allows plate 109 to remain motionless during characterization, thereby providing several benefits. First, limiting the motion of plate 109 limits the possibility of liquid within an individual sample well 123 from splashing out of the well. Loss of liquid through splashing can alter the chemical reaction not only of the sample well from which liquid was lost, but also in adjacent sample wells that may receive some of the splashed liquid. Second, by not requiring movement of plate 109 during a reading, the amount of mixing within sample wells 123 can be controlled. For example, it may be desirable to provide no additional mixing after each of the components of a multi-component sample has been placed within a sample well. Alternatively, it may be desirable to provide mixing by controllably shaking plate 109 for a specific period of time with a specific vibrational amplitude and frequency. In this instance plate 109 can be coupled to a vibration table or other mechanism.

Depending upon the design, location, and output characteristics of source 103; the design, location, and detection characteristics of detector 107; and the transmission characteristics of the bottom surface of sample wells 123; head assembly 101 can be used in a variety of different testing schemes. In the preferred embodiment of the invention, light 105 from source 103 passes through the bottom surface of the sample well, through the sample within an individual sample well, and is detected by detector 107, thereby providing a measure of the absorption characteristics of the sample. Alternatively, the locations of source 103 and detector 107 can be exchanged, thus locating source 103 in upper arm 113 and detector 107 in lower arm 111. The head assembly can also be used in instruments designed to determine the fluorescence or luminescence of a sample.

Figure 2:
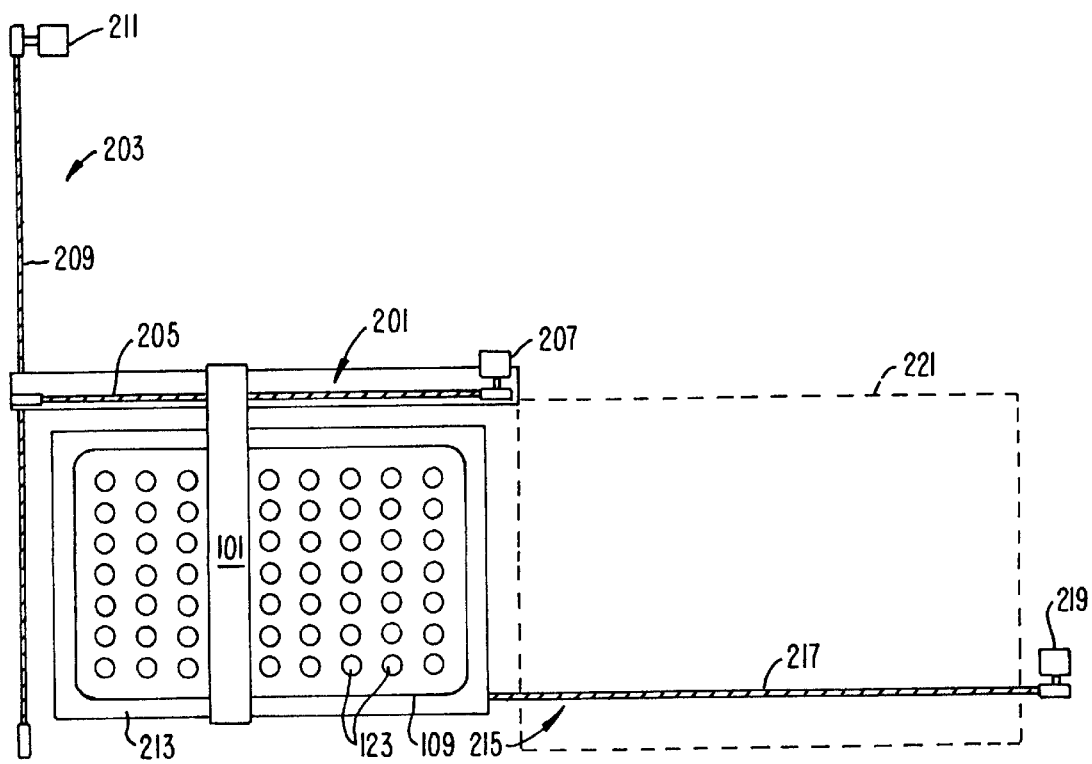
FIG. 2 is an illustration of an instrument utilizing a read head assembly according to the invention.

FIG. 2 is an illustration of an instrument 200 utilizing read head assembly 101. Head assembly 101 is coupled to an x-axis scanning system 201 and a y-axis scanning system 203, thus allowing the source and detection portions of the head assembly to be used to analyze the samples contained in every sample well 123 of sample plate 109. As shown, x-axis scanning system 201 is comprised of a belt and pulley system 205 and a drive motor 207. Similarly, y-axis scanning system 203 is comprised of a belt and pulley system 209 and a drive motor 211. Although belt and pulley systems are used in the preferred embodiment of the invention, it should be apparent to one of skill that other scanning systems could be used such as gear drive systems, etc.

In at least one embodiment of the invention, sample 109 is held on a sample plate carrier 213. Plate carrier 213 preferably uses a sample holding fixture that is either adjustable or can be used with various sample plate adaptors, thus allowing a variety of different sample plates (e.g., 6, 12, 24, 48, 96, and 384 well microplates, etc.) to be used with instrument 200. Although plate carrier 213 can be designed to accommodate any size sample plate, preferably it is designed to accommodate at least a standard 96 well sample plate (i.e., 130 millimeters by 95 millimeters).

Plate carrier 213 can be coupled to a second x-axis transport mechanism 215, mechanism 215 using either a belt and pulley system 217 and drive motor 219 as shown, or another type of transport mechanism. System 215 is used to move plate carrier 213, and thus sample plate 109, into position for characterization by assembly 101. System 215 can also be used to move sample plate 109 into another preparation and/or testing region 221. In the preferred embodiment, region 221 is an incubator that can be used to control the temperature and/or humidity of the sample plate. Preferably the incubator is programmable from ambient to 42° C. in 0.2° C. increments and maintains a temperature variation across the sample plate of less than or equal to 0.5° C.

Figure 3:
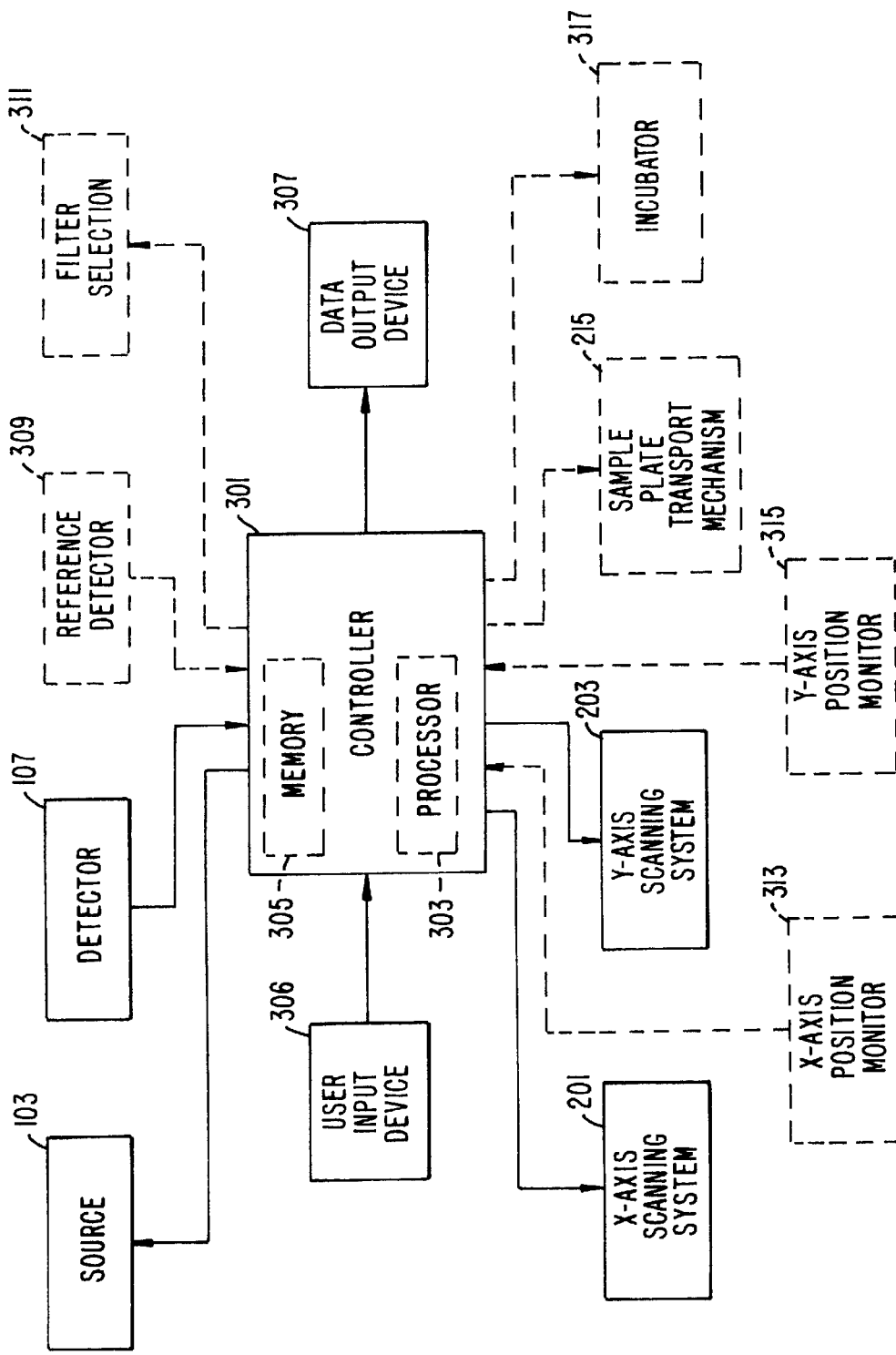
FIG. 3 schematically illustrates the control system utilized in the preferred embodiment of the invention.

FIG. 3 schematically illustrates the control system utilized in the preferred embodiment of the invention. A controller 301 is used to control the various functions of the instrument, ranging from sample scanning to data processing. Controller 301 may utilize one or more processors 303 and contain memory 305 for storing instructions and data. Controller 301 preferably controls all aspects of head assembly 101 including source 103, detector 107, and x- and y-axis scanning systems 201 and 203, respectively. The user inputs any required system operation parameters (e.g., sample plate type, well size and number, well spacing, scan mode, number of measurements to be made per sample well, whether or not to average readings, etc.) using a user input device 306 such as a keyboard, touchscreen, etc. Controller 301 outputs the data with a data output device 307, e.g., a printer, plotter, or monitor.

In addition to controlling the instrument as outlined above, controller 301 can also be used to control other aspects of the instrument. For example, if read head assembly 101 includes a reference detector 309, controller 301 preferably receives the output from detector 309, thus allowing relative measurements to be made. Additionally, assembly 101 can include one or more filter wheels 311 to control the wavelength of radiation from source 103 impinging upon the samples and/or the wavelengths detected by detector 107. Controller 301 can also be coupled to x- and y-axis position monitors 313 and 315, respectively, these monitors providing sample plate carrier location feedback to the control system. Lastly, if the instrument includes multiple testing and/or preparation regions as briefly described above, controller 301 can be used to control sample plate transport mechanism 215 as well as the additional region (e.g., incubation chamber humidity and temperature control 317).

Figure 4:
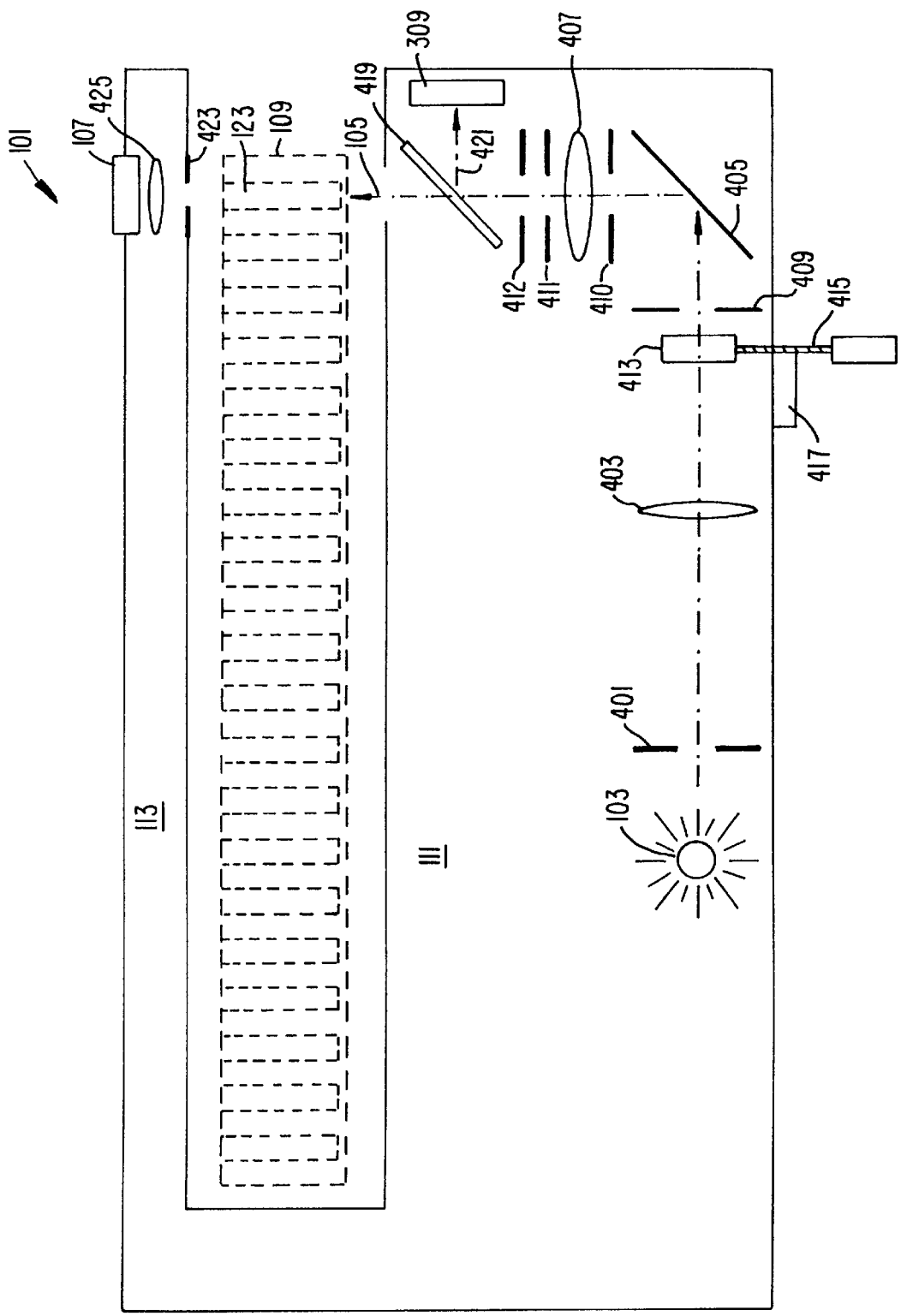
FIG. 4 is a schematic representation of the cross-section of the preferred embodiment of the read head assembly.

FIG. 4 is a cross-sectional view of the preferred embodiment of read head assembly 101. In this embodiment read head assembly 101 is designed to analyze a samples absorption characteristics. Assembly 101 includes source 103, preferably a xenon flash lamp. Other types of sources (e.g., laser sources) can also be used with the invention, either mounted within assembly 101 as in the preferred embodiment or mounted separately from assembly 101 and optically coupled to the assembly using optical fibers or other means. The radiation from source 103 is conditioned prior to impinging upon a sample, thus insuring that the beam has a sufficiently narrow beam diameter. In the illustrated embodiment, the output of source 103 passes through an aperture 401 and a lens 403 prior to being reflected by mirror 405 along path 105. A second lens 407 further conditions the beam prior to its emergence from head assembly 101. In the preferred embodiment lens 401 is a convex-convex lens with a diameter of 20 millimeters and a focal length of 20 millimeters and lens 407 is a collimating plano-convex lens with a diameter of 10 millimeters and a focal length of 20 millimeters. This embodiment also includes apertures 409–412 with 2, 1.5, 1.5, and 0.3 millimeter diameter apertures, respectively.

In at least one embodiment of the invention, the output of source 103 is tunable using a filter 413 such as a bandpass filter, a cutoff filter, etc. Filter 413 is selected from a series of filters, preferably contained in a filter wheel 415. The selection of filter 413 from filter wheel 415 is preferably automated using a filter wheel motor 417 coupled to processor 301. Source wavelength selection can also be accomplished using a diffraction grating either mounted within head assembly 101 or, for the case of an externally mounted source, mounted separate from the head assembly.

Prior to exiting from lower arm 111, output beam 105 preferably passes through a beam splitter 419, reflecting a portion of light 421 towards reference detector 309. Preferably beam splitter 419 is a quartz plate, reflecting approximately 20 percent of the incident light and transmitting approximately 80 percent of the incident light. Detector 309 is preferably a photodiode. Detector 309 is used to monitor variations in the output of source 103.

Shown in phantom in FIG. 4 is a representative sample plate 109 and representative sample wells 123. In this embodiment of the invention, light beam 105, exiting lower arm 111 after passing through beam splitter 417, passes through the sample well 123 being characterized. The light in beam 105 that is not absorbed by the sample within the well, or by the bottom surface of the well, passes through an aperture 423 and is focussed by a lens 425 onto detector 107. Preferably aperture 423 is 4.5 millimeters in diameter, lens 425 is a 6 millimeter diameter ball lens, and detector 107 is a silicon photodiode. In addition to monitoring output variations from source 103, the ratio of the output of reference detector 309 to the output of measurement detector 107 can be used to determine the relative absorption of a sample. In the preferred embodiment of the invention, the instrument is capable of measuring optical densities (i.e., OD) between 0.000 and 4.000, outputting this information via data output device 307.

Figure 5:
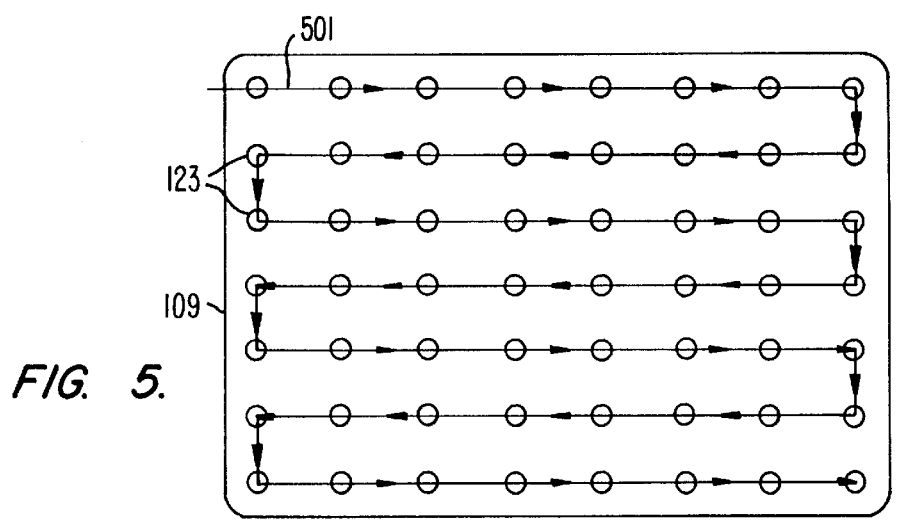
FIG. 5 is an illustration of the preferred scanning pattern.
Figure 6:
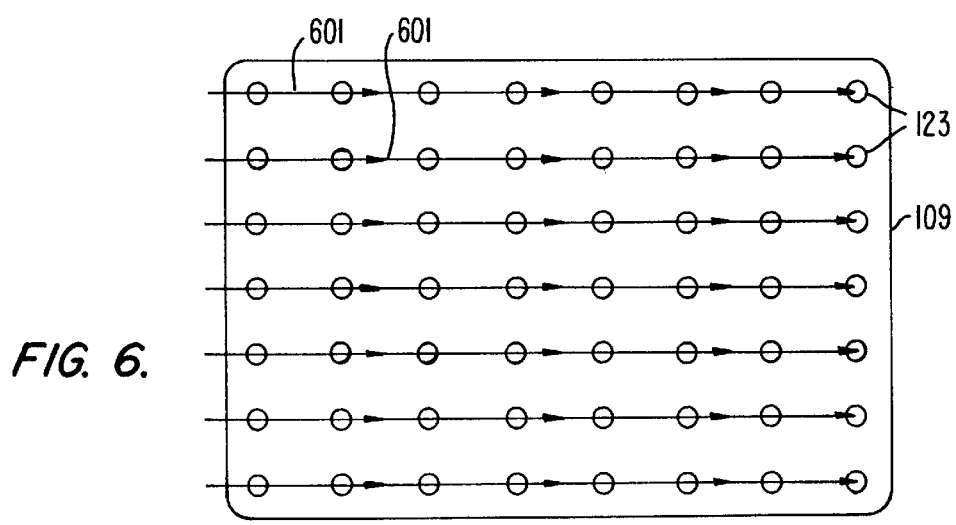
FIG. 6 is an illustration of an alternative scanning pattern.

As noted, an instrument designed in accordance with the present invention can be used to determine various sample characteristics such as fluorescence and luminescence, although in the preferred embodiment it is used to determine the absorption of samples. Additionally, the instrument can be designed to scan a sample plate in a number of ways. In the preferred embodiment, read head assembly 101 raster scans sample plate 109 in a serpentine pattern 501 as illustrated in FIG. 5. This is the preferred scan mode as it allows each sample to be characterized rapidly and efficiently. Alternatively as shown in FIG. 6, all of the rows (or columns) can be scanned in the same direction 601. In a third alternative, the user can program controller 301 to move head assembly 101 to specific sample wells (e.g., a subset of all of the samples) and/or to interrogate the sample wells in a specific order.

Figure 7:
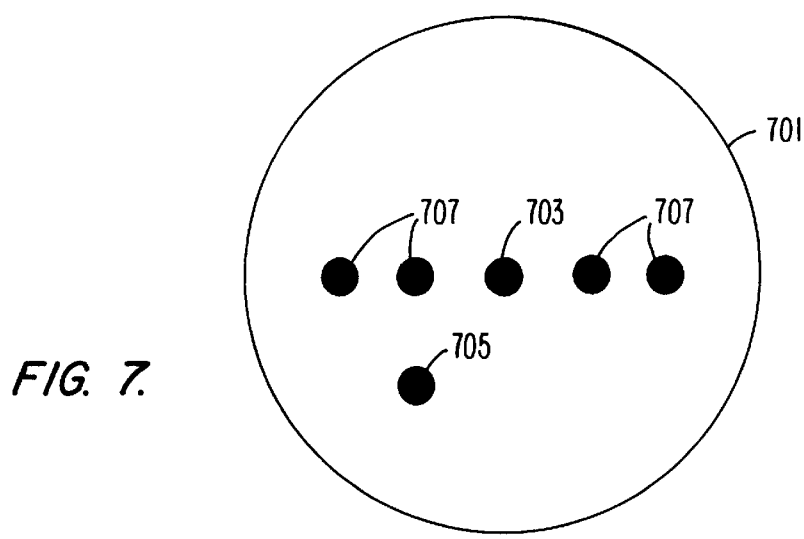
FIG. 7 is a cross-sectional view of a single sample well, illustrating various interrogation techniques in accordance with the present invention.

FIG. 7 is a cross-sectional view of a single sample well 701, representative of one of a plurality of sample wells in a sample plate. In accordance with the present invention, sample well 701 can be interrogated in a variety of ways. First, a single measurement can be made at a single location 703. The volume of the sample within well 701 that is interrogated in this measurement depends upon the diameter of light beam 105 as it passes through the sample. It should be understood that although location 703 is shown in the center of well 701, other locations can also be used (e.g., location 705) that are off-center. Second, multiple locations 707 can be interrogated. It should be understood that both fewer and greater numbers of locations 707 can be used with the invention and that the locations shown are only meant to be illustrative. Preferably the user can preset the number of locations as well as the pattern of locations (e.g., circular or square pattern). The measured value (e.g., OD) for each location can be reported or an average value can be determined and reported. Preferably in either sample interrogation mode, controller 301 causes source 103 to flash a single time for each measurement being performed. Those of skill in the art will understand that other methods of controlling source 103 are equally applicable to the present invention.

As will be understood by those familiar with the art, the present invention may be embodied in other specific forms without departing from the spirit or essential characteristics thereof. Accordingly, the disclosures and descriptions herein are intended to be illustrative, but not limiting, of the scope of the invention which is set forth in the following claims.

What is claimed is:

1. A sample plate scanning system, comprising:
    a head assembly with a first arm portion, a second arm portion, and a connecting portion rigidly coupling said first and second arm portions;
    a first transport system coupled to said head assembly for scanning said head assembly along a first axis;
    a second transport system coupled to said head assembly for scanning said head assembly along a second axis, said second axis substantially orthogonal to said first axis;
    a sample plate holder for holding a sample plate in a sample reading position, wherein said sample plate is interposed between said first arm portion and said second arm portion when said sample plate is in said sample reading position;

a source of radiation coupled to said first arm portion, wherein said radiation is directed along a first optical path from said first arm portion towards said second arm portion; and a detector coupled to said second arm portion, wherein said detector detects radiation along said first optical path, said detector outputting a signal corresponding to an amplitude associated with said detected radiation.

2. The sample plate scanning system of claim 1, wherein said source of radiation comprises a xenon lamp.

3. The sample plate scanning system of claim 2, wherein said xenon lamp is mounted within said first arm portion.

4. The sample plate scanning system of claim 1, said radiation source further comprising at least one collimating lens and at least one aperture, said radiation from said source passing through said at least one collimating lens and said at least one aperture prior to exiting said first arm portion towards said second arm portion along said first optical path.

5. The sample plate scanning system of claim 3, further comprising:

a first lens mounted within said first arm portion, wherein said radiation traveling along a second optical path passes through said first lens;

a turning mirror mounted within said first arm portion, wherein said radiation passing through said first lens along said second optical path is directed along said first optical path by said turning mirror; and a second lens mounted within said first arm portion, wherein said radiation directed by said turning mirror along said first optical path passes through said second lens prior to exiting said first arm portion towards said second arm portion along said first optical path.

6. The sample plate scanning system of claim 5, wherein said first lens is a convex-convex lens with a first focal length of 20 millimeters and said second lens is a plano-convex lens with a second focal length of 20 millimeters.

7. The sample plate scanning system of claim 5, further comprising:

a first aperture interposed between said first and second lenses; and a second aperture following said second lens, wherein radiation passes through said second aperture prior to exiting said first arm portion towards said second arm portion along said first optical axis.

8. The sample plate scanning system of claim 1, further comprising an optical filter, wherein radiation from said source passes through said optical filter prior to exiting said first arm portion towards said second arm portion long said first optical path, wherein said optical filter limits said radiation to a predetermined wave length band.

9. The sample plate scanning system of claim 1, further comprising:

a plurality of optical filters, wherein each of said plurality of optical filters passes a predetermined band of wavelengths; and an optical filter transport system coupled to said plurality of optical filters and mounted to said first arm portion, wherein said optical filter transport system interposes a selected one of said plurality of optical filters between said radiation source and a first arm portion exit aperture.

10. The sample plate scanning system of claim 1, further comprising:

a beam splitter mounted within said first optical path, wherein a first portion of radiation passes through said beam splitter and continues along said first optical path and exits said first arm portion; and a reference detector, wherein a second portion of radiation is reflected by said beam splitter along a second optical path, wherein said reference detector detects radiation along said second optical path, said reference detector outputting a reference signal corresponding to a reference amplitude of said radiation detected along said second optical path.

11. The sample plate scanning system of claim 1, further comprising:

a beam splitter mounted within said first arm portion, wherein a first portion of said radiation from said source is reflected and directed along said first optical path; and a reference detector, wherein a second portion of radiation is transmitted by said beam splitter along a second optical path, wherein said reference detector detects radiation along said second optical path, said reference detector outputting a reference signal corresponding to a reference amplitude of said radiation detected along said second optical path.

12. The sample plate scanning system of claim 1, wherein said detector is a photodiode mounted within said second arm portion.

13. The sample plate scanning system of claim 1, further comprising a lens mounted within said second arm portion, wherein said lens collects at least a portion of said radiation passing along said first optical path, and wherein said lens focuses said collected radiation onto said detector.

14. The sample plate scanning system of claim 1, further comprising an aperture mounted to said second arm portion, wherein at least a portion of said radiation passing along said first optical path passes through said aperture prior to being detected by said detector.

15. The sample plate scanning system of claim 1, further comprising a controller coupled to said first and second transport systems and controlling a scan pattern associated with said head assembly.

16. The sample plate scanning system of claim 1, further comprising a third transport system, said third transport system coupled to said sample plate holder, said third transport system moving said sample plate holder from a first position to a second position, wherein said first position is said sample reading position.

17. The sample plate scanning system of claim 16, wherein said second position is a sample plate loading position.

18. A sample plate scanning system, comprising:

a head assembly with a first arm portion, a second arm portion, and a connecting portion rigidly coupling said first and second arm portions;

a first transport system coupled to said head assembly for scanning said head assembly along a first axis;

a second transport system coupled to said head assembly for scanning said head assembly along a second axis, said second axis substantially orthogonal to said first axis;

a controller coupled to said first and second transport systems and controlling a scan pattern associated with said head assembly;

a sample plate holder for holding a sample plate in a sample reading position, wherein said sample plate is interposed between said first arm portion and said second arm portion when said sample plate is in said sample reading position;

a source of radiation mounted within said first arm portion, said source of radiation comprising:
  a lamp emitting said radiation;
  a first lens, wherein said radiation from said lamp passes through said first lens;
  a turning mirror, wherein said radiation passing through said first lens is directed along a first optical path by said turning mirror; and
  a second lens, wherein said radiation directed by said turning mirror along said first optical path passes through said second lens prior to exiting said first arm portion towards said second arm portion along said first optical path; and a detection system mounted within said second arm portion, said detection system comprising:
  a detector; and
  a third lens, wherein said third lens collects at least a portion of said radiation passing along said first optical path from said first arm portion, wherein said lens focuses said collected radiation onto said detector, wherein said detector outputs a signal corresponding to an amplitude associated with said detected radiation.

19. The sample plate scanning system of claim 18, further comprising:

a plurality of optical filters, wherein each of said plurality of optical filters passes a predetermined band of wavelengths; and an optical filter transport system coupled to said plurality of optical filters and mounted to said first arm portion, wherein said optical filter transport system interposes a selected one of said plurality of optical filters between said lamp and a first arm portion exit aperture.

20. The sample plate scanning system of claim 18, further comprising:

a beam splitter mounted within said first optical path and interposed between said second lens and a first arm portion exit aperture, wherein a first portion of radiation passes through said beam splitter and continues along said first optical path and through said first arm portion exit aperture; and a reference detector, wherein a second portion of radiation is reflected by said beam splitter along a second optical path, wherein said reference detector detects radiation along said second optical path, said reference detector outputting a reference signal corresponding to a reference amplitude of said radiation detected along said second optical path.

21. The sample plate scanning system of claim 18, wherein said controller is coupled to said detector, said controller processing said detector output signal.

* * * * *